US009333260B2

(12) United States Patent
Pellico et al.

(10) Patent No.: US 9,333,260 B2
(45) Date of Patent: May 10, 2016

(54) COMPOSITIONS AND METHODS FOR ENZYMATIC TREATMENT OF LUNG DISORDERS

(75) Inventors: Michael A. Pellico, Rancho Dominguez, CA (US); Pamela Bosco, Westmont, IL (US)

(73) Assignee: Laclede, Inc., Rancho Dominguez, CA (US)

( * ) Notice: Subject to any disclaimer, the term of this patent is extended or adjusted under 35 U.S.C. 154(b) by 1354 days.

(21) Appl. No.: 12/299,897

(22) PCT Filed: May 10, 2007

(86) PCT No.: PCT/US2007/068688
§ 371 (c)(1),
(2), (4) Date: Mar. 3, 2010

(87) PCT Pub. No.: WO2007/134180
PCT Pub. Date: Nov. 22, 2007

(65) Prior Publication Data

US 2010/0150897 A1 Jun. 17, 2010

Related U.S. Application Data

(60) Provisional application No. 60/799,535, filed on May 10, 2006.

(51) Int. Cl.

| | |
|---|---|
| ***A61K 31/573*** | (2006.01) |
| ***A61K 38/40*** | (2006.01) |
| ***A61K 38/44*** | (2006.01) |
| ***A61K 38/47*** | (2006.01) |
| ***A61K 45/06*** | (2006.01) |

(52) U.S. Cl.
CPC ............... *A61K 45/06* (2013.01); *A61K 31/573* (2013.01); *A61K 38/40* (2013.01); *A61K 38/44* (2013.01); *A61K 38/443* (2013.01); *A61K 38/47* (2013.01); *C12Y 101/03004* (2013.01); *C12Y 101/03009* (2013.01); *C12Y 101/03017* (2013.01); *C12Y 111/01007* (2013.01); *C12Y 111/02002* (2013.01)

(58) Field of Classification Search
None
See application file for complete search history.

(56) References Cited

U.S. PATENT DOCUMENTS

| | | | |
|---|---|---|---|
| 4,370,199 | A | 1/1983 | Orndorff et al. |
| 4,576,817 | A | 3/1986 | Montgomery et al. |
| 5,503,853 | A | 4/1996 | Bollen et al. |
| 5,607,681 | A | 3/1997 | Galley et al. |
| 5,629,024 | A | 5/1997 | Kessler et al. |
| 5,639,481 | A | 6/1997 | Kessler et al. |
| 6,214,339 | B1 | 4/2001 | Pellico et al. |
| 2002/0172645 | A1 | 11/2002 | Conner |
| 2003/0143191 | A1 | 7/2003 | Bell et al. |
| 2003/0143214 | A1 | 7/2003 | Pellico et al. |
| 2004/0235946 | A1 | 11/2004 | Ott |
| 2005/0147607 | A1 | 7/2005 | Reed |

FOREIGN PATENT DOCUMENTS

| | | |
|---|---|---|
| EP | 0307376 | 3/1989 |
| JP | 2002322088 | 11/2002 |
| JP | 2006503865 | 2/2006 |
| WO | 9922597 | 5/1999 |

OTHER PUBLICATIONS

Thomas et al. "Peroxidase Antimicrobial System of Human Saliva: Requirements for Accumulation of Hypothiocyanite," J. Dent Res. (1981) 60(4):785-796.
Hydrogen Peroxide ATSDR; p. 1-20.

*Primary Examiner* — Lisa J Hobbs
(74) *Attorney, Agent, or Firm* — Lewis Kohn & Walker LLP; David M. Kohn

(57) ABSTRACT

A therapeutic composition for the treatment of lung diseases or disorders and diseases or disorders of the airway passages including pneumonia, acute respiratory failure, and acute respiratory distress syndrome is based on the generation of a biocidal anion by an enzymatic reaction catalyzed by a peroxidase. The peroxide utilized by the peroxidase enzyme can be endogenous or can be generated by the action of an oxidase enzyme on a suitable substrate.

9 Claims, No Drawings

COMPOSITIONS AND METHODS FOR ENZYMATIC TREATMENT OF LUNG DISORDERS

CROSS-REFERENCES

This application claims priority from Provisional Application Ser. No. 60/799,535 by Michael Pellico and Pamela Bosco, entitled "Compositions and Methods for Enzymatic Treatment of Lung Disorders," filed May 10, 2006, which is incorporated herein in its entirety by this reference.

BACKGROUND OF THE INVENTION

This invention relates to an enzymatic treatment for patients suffering from pneumonia and other lung and sinus infections.

Today, ventilator-induced pneumonia is one of the leading causes of hospital deaths due to infections. Such infections are frequently referred to as nosocomial infections.

*Mycoplasma pneumoniae* is resistant to many antibiotics such as penicillin, cephalosporins, and vancomycin. *M. pneumoniae* causes a pneumonia often called "walking pneumonia" or "primary atypical pneumonia."

Other cases of pneumonia can be caused by a number of species of bacteria, including, but not limited to, *Streptococcus* species, *Staphylococcus* species, *Pseudomonas* species, *Haemophilus* species, and chlamydia.

The disease can be divided into two forms, bronchial pneumonia and lobar pneumonia.

Multiple antibiotic resistant forms of *Streptococcus pneumoniae* that emerged in the early 1970s in Papua New Guinea and South Africa were thought to be flukes, but multiple antibiotic resistance now covers the globe and has rapidly increased since 1995. Increases in penicillin resistance have been followed by resistance to cephalosporins and by multi-drug resistance. The incidence of resistance to penicillin increased from <0.02% in 1987 to 3% in 1994 to 30% in some communities in the United States and 80% in regions of some other countries in 1998. Resistance to other antibiotics has emerged simultaneously: 26% resistant to trimethoprim/sulfa, 9% resistant to cefotaxime, 30% resistant to cefotaxime, 30% resistant to macrolides, and 25% resistant to multiple drugs. Resistant organisms remain fully virulent.

Various peroxidases play an important role in protecting mammals from infections. The most important peroxidases are lactoperoxidase, myeloperoxidase, and eosinophil peroxidase. These various peroxidases have been found in saliva, milk, vaginal secretions, and recently in the lungs and sinuses. Peroxidase enzymes scavenge potentially toxic hydrogen peroxide and thus are also an important part of the body's defense against free radical damage.

In the mouth there is a need for defense against hydrogen peroxide because hydrogen peroxide is formed by bacteria colonizing the mucous membrane. In saliva, lactoperoxidase detoxifies hydrogen peroxide in the present of thiocyanate by converting it into hypothiocyanite ($^{-}OSCN$), molecular oxygen($O_2$), and water. The hypothiocyanite ion then inhibits hydrogen-peroxide-producing bacteria. Lactoperoxidase thus forma a key part of the antibacterial defenses of saliva.

In milk the second most abundant protein is lactoperoxidase. In 1924 Hanssen suggested that the bacterial properties of milk against bacteria such as *Salmonella* species, including *S. paratyphosa*, are the results of its peroxidase activity. Since then numerous studies have confirmed its activity. From 1976 onwards Thomas and collaborators established $^{-}OSCN$-HOSCN as an oxidizing agent for bacterial sulfhydryls and proteins.

In the study "Isolation and Characterization of a Peroxidase from the Airway," Salathe and Holderby showed that a peroxidase scavenges hydrogen peroxide from airways. Hydrogen peroxide is an important mediator of airway inflammation. They showed that this peroxidase was similar to lactoperoxidase but was different from other peroxidases including myeloperoxidase, eosinophil peroxidase, and glutathione peroxidases. As in the oral cavity and vagina, the peroxidase controls free radicals and catalyzes the function of biocidal compounds. This is especially important during times of infection. For example, the bacterium *Streptococcus pneumoniae* produces large amounts of hydrogen peroxide which inflames lung tissue. The authors designated the peroxidase activity found in tracheal secretions airway peroxidase (APO). This peroxidase, like lactoperoxidase in saliva, is likely to be biocidal against bacteria, fungi, and viruses and to act as a scavenger of hydrogen peroxide during airway inflammation. In a study published in 2000 entitled "The Lactoperoxidase System Functions in Bacterial Clearance of Airways" by Gersen, Sabater, and Scuri, the airway peroxidase was shown to be identical to milk lactoperoxidase. Their data also showed that the lactoperoxidase system is a major contributor to airway defense systems. As described earlier, the lactoperoxidase system is a significant free radical scavenger. Studies have shown that *S. pneumoniae* infections are associated with significant damage to the alveolar epithelium.

As in other parts of the body, the lactoperoxidase system, along with other peroxidase, lysozyme, and lactoferrin, usually works quite well in purging the body of harmful organisms. However, in times of severe infections, this protective system can be overwhelmed. Besides infections, another potential cause of high levels of hydrogen peroxide is found in patients suffering from acute respiratory failure or from ARDS (acute respiratory distress syndrome). Patients with acute respiratory failure or ARDS exhibit higher concentrations of hydrogen peroxide than control patients.

Several patents describe the use of an enzymatic system to produce an antibacterial or biocidal effect.

U.S. Pat. No. 4,370,199 to Orndorff (1983) discloses a method of killing and inhibiting the growth of microorganisms in industrial process streams by the addition of an enzymatically catalyzed biocide system which utilized a plant dehydrogenase enzyme such as horseradish peroxidase in the presence of an oxidant such as hydrogen peroxide to oxidize a halide salt such as potassium iodide or sodium chloride to produce an oxidation product that is toxic to microorganisms.

U.S. Pat. No. 4,150,113 to Hoogendoorn et al. (1979) and U.S. Pat. No. 4,178,362 to Hoogendoorn et al. (1979) disclose, respectively, an enzymatic toothpaste and an enzymatic chewable dentifrice containing glucose oxidase which acts on glucose present in saliva and tooth plaque to produce hydrogen peroxide. The patentees note that oral bacteria, through enzyme systems having sulfhydryl groups, effect glycolysis of food products containing sugars and point out that lactoperoxidase, which is present in saliva, provides the means for transferring oxygen from hydrogen peroxide to oral bacteria resulting in the oxidation of the sulfhydryl-group-containing enzymes into inactive enzymes in which the sulfhydryl groups have been oxidized into disulfide groups. It is further disclosed that the dentifrice can be formulated with potassium thiocyanate.

U.S. Pat. No. 4,269,822 to Pellico et al. (1981) discloses an antiseptic dentifrice containing an oxidizable amino acid substrate and an oxidoreductase enzyme specific to the substrate for producing hydrogen peroxide and ammonia upon oral application of the dentifrice, with pre-application stability being maintained by limiting the quantity of any water present in the dentifrice.

U.S. Pat. No. 4,537,764 to Pellico et al. (1985) discloses an enzymatic dentifrice containing β-D-glucose and glucose oxidase for producing hydrogen peroxide upon oral application of the dentifrice, with pre-application stability being maintained by limiting any water in the dentifrice to not more than about 10% by weight based on the weight of the dentifrice.

U.S. Pat. No. 4,576,817 to Montgomery et al. (1986) discloses enzymatic bandages and pads, for body contact applications, containing, for example, glucose oxidase which catalyzes a reaction between β-D-glucose, water, and oxygen in serum to produce hydrogen peroxide. The bandages and pads can further contain a peroxidase and an oxidizable salt such as thiocyanate, chloride, or iodide salts of sodium or potassium which, in the presence of hydrogen peroxide and peroxidase, are oxidized to hypothiocyanite, hypochlorite, and hypoiodite, respectively, that function as bacterial inhibitors.

U.S. Pat. No. 4,564,519 to Pellico et al. (1986) discloses a di-enzymatic chewable dentifrice which, contains, for example, glucose and glucose oxidase for producing hydrogen peroxide upon chewing the dentifrice and further contains a thiocyanate salt and lactoperoxidase for reacting with the hydrogen peroxide to produce a hypothiocyanite bacterial inhibitor, with pre-application stability being maintained by limiting any unbound water in the chewable dentifrice to an amount of not more than about 1.0 weight percent, and by limiting the total water, bound and unbound, to not more than about 10 weight percent.

U.S. Pat. No. 4,578,365 to Pellico et al. (1986) discloses a di-enzymatic dentifrice which contains, for example, glucose and glucose oxidase for producing hydrogen peroxide upon oral application of the dentifrice and further contains a thiocyanate salt and lactoperoxidase for reacting with the hydrogen peroxide to produce a hypothiocyanite, with pre-application stability being maintained by limiting any water in the dentifrice to not more than about 10 weight percent based on the weight of the dentifrice.

U.S. Pat. No. 4,617,190 to Montgomery (1986) discloses enzymatic powder milk that contains, for example, glucose, glucose oxidase, a peroxidase, and potassium iodide for producing hypoiodite, an anionic bacterial inhibitor in the reconstituted milk.

U.S. Pat. No. 5,336,494 to Pellico (1994) discloses an orally chewable, enzymatically coated pet product, which contains, for example, β-D-glucose and glucose oxidase for producing hydrogen peroxide upon oral chewing of the product, and can further contain a peroxidase and an alkali metal salt of an oxygen accepting anion such as potassium iodide for reaction with hydrogen peroxide to produce hypoiodite, an anionic bacterial inhibitor.

U.S. Pat. No. 5,453,284 to Pellico (1995) discloses an aqueous enzymatic dentifrice having a water content in excess of 10 weight percent and which contains, for example, β-D-glucose and glucose oxidase for producing hydrogen peroxide upon oral application of the dentifrice and can further contain a peroxidase and an oxidizable alkali metal salt such as the thiocyanate, chloride, or iodide salt of sodium or potassium for reacting with hydrogen peroxide to produce an anionic bacterial inhibitor. Pre-application stability is maintained by the addition of a water-soluble thickener in a quantity such that the dentifrice has a viscosity from about 800 to about 75,000 centipoises.

Accordingly, there is a need for compositions and methods utilizing enzymatic activity that can be delivered to the respiratory tract, including the lungs, to combat infection and inflammation by catalyzing the breakdown of peroxides such as hydrogen peroxide. Although there are a number of methods and compositions known that include therein the enzymatic breakdown of hydrogen peroxide or other peroxide, these methods and compositions do not provide a means of delivery of enzymatic activity to the respiratory tract in a form that allows the enzymatic activity to combat infection and inflammation.

SUMMARY OF THE INVENTION

One embodiment of the present invention is a therapeutic composition comprising:

(1) a first component comprising:

(a) one of:

(i) an oxidoreductase enzyme that produces hydrogen peroxide by catalyzing the oxidation of a substrate for which the oxidreductase enzyme is specific, the first component comprising a sufficient quantity of the oxidoreductase enzyme that a quantity of hydrogen peroxide sufficient to react with a peroxidase is produced; and (ii) a substrate that is oxidizable in a reaction catalyzed by the oxidoreductase enzyme in a sufficient quantity that a quantity of hydrogen peroxide sufficient to react with a peroxidase is produced;

(b) a peroxidase enzyme that catalyzes a reaction between hydrogen peroxide and a salt that acts as an oxygen acceptor and is capable of reacting with hydrogen peroxide to form a biocide, the peroxidase enzyme being present in a sufficient quantity such that the biocide is produced in a therapeutically effective concentration; and (c) an aqueous or nonaqueous medium in which the enzymes and the oxidizable substrate, if present, are stable; and (2) a second component comprising:

(a) the other of the oxidoreductase enzyme and the substrate that is oxidizable in a reaction catalyzed by the oxidoreductase enzyme that is not present in (1); and (b) a salt that acts as an oxygen acceptor and is capable of reacting with hydrogen peroxide to form a biocide in a quantity sufficient to form a therapeutically effective concentration of the biocide; and (c) an aqueous or nonaqueous medium in which the other of the oxidoreductase enzyme and the oxidizable substrate and the salt that acts as an oxygen acceptor are stable, with the proviso that one of the media of the first component and the second component is aqueous.

In one alternative, the medium of (1) and the medium of (2) are both aqueous. In another alternative, one of the media of (1) and (2) is aqueous and the other of the media of (1) and (2) is nonaqueous.

Typically, the oxidoreductase enzyme is selected from the group consisting of glucose oxidase, galactose oxidase, urate oxidase, choline oxidase, D-amino acid oxidase, O-glutamate oxidase, glycine oxidase, glycolic oxidase, L-sorbose oxidase, alcohol oxidase, and amine oxidase. Typically, the peroxidase enzyme is selected from the group consisting of lactoperoxidase, horseradish peroxidase, myeloperoxidase, eosinophil peroxidase, and glutathione peroxidase. The composition can further comprise an additional peroxidase enzyme.

Typically, the salt that acts as an oxygen acceptor and is capable of reacting with hydrogen peroxide to form a biocide is an alkali metal salt of an anion selected from the group consisting of thiocyanate, iodate, and chlorate. Typically, the alkali metal salt is selected from the group consisting of a sodium salt and a potassium salt.

The composition can further comprise an effective amount of an inhibitor that is specific for catalase. Typically, the inhibitor that is specific for catalase is a salt of ascorbic acid. Typically, the salt of ascorbic acid is selected from the group consisting of sodium ascorbate, potassium ascorbate, calcium ascorbate, ascorbyl palmitate, and mixtures thereof. The composition can further comprise an iron salt; typically, the iron salt is selected from the group consisting of ferrous sulfate, ferrous chloride, and ferrous iodide.

The composition can further comprise a quantity of an aminohexose effective in increasing the yield or accumulation of biocide formed. Typically, the aminohexose is an aminoglucose. Typically, the aminoglucose is selected from glucosamine, N-acetylglucosamine, and mixtures thereof.

In the composition, the media can be each independently selected from the group consisting of water, glycerol, sorbitol, propylene glycol, and mixtures thereof, with the proviso that at least one of the media includes a substantial proportion of water.

The composition can further comprise a buffering agent. Typically, the buffering agent is selected from the group consisting of sodium stearate, potassium stearate, and calcium stearate.

The composition can further comprise any or all of lysozyme, lactoferrin, or a steroid. Typically, the steroid is selected from the group consisting of hydrocortisone, beclomethasone, budenoside, ciclesonide, flunisolide, fluticasone, methylprednisolone, prednisolone, prednisone, and triamcinolone, and the salts, solvates, analogues, congeners, bioisosteres, hydrolysis products, metabolites, precursors, and prodrugs thereof. Preferably, the steroid is hydrocortisone.

Another embodiment of a therapeutic composition according to the present invention is a composition comprising:

(1) a peroxidase enzyme that catalyzes a reaction between hydrogen peroxide and a salt that acts as an oxygen acceptor and is capable of reacting with hydrogen peroxide to form a biocide, the peroxidase enzyme being present in a sufficient quantity such that the biocide is produced in a therapeutically effective concentration;

(2) a salt that acts as an oxygen acceptor and is capable of reacting with hydrogen peroxide to form a biocide in a quantity sufficient to form a therapeutically effective concentration of the biocide; and (3) an aqueous medium in which the peroxidase enzyme and the salt that acts as an oxygen acceptor are stable.

Particular embodiments of the invention include, but are not limited to, a therapeutic composition selected from the group of:

(1) a composition comprising:
(a) a first component comprising, per 100 grams:
(i) about 80 g of water;
(ii) about 20 g of glycerol; and
(iii) about 5.0 IU of lactoperoxidase; and
(b) a second component comprising, per 100 grams:
(i) about 100 g of water; and
(ii) about 0.01 millimole of potassium thiocyanate;
(2) a composition comprising:
(a) a first component comprising, per 100 grams:
(i) about 95.0 g of water;
(ii) about 5.0 g of propylene glycol; and
(iii) about 25.0 IU of lactoperoxidase; and
(b) a second component comprising, per 100 grams:
(i) about 100 g of water; and
(ii) about 0.1 millimole of potassium iodate;
(3) a composition comprising:
(a) a first component comprising, per 100 grams:
(i) about 50.0 g of water;
(ii) about 100.0 IU of lactoperoxidase;
(iii) about 49.5 g of glycerol; and
(iv) about 0.5 g of citric acid;
(b) a second component comprising, per 100 grams:
(i) about 100 g of water; and
(ii) about 1.0 millimole of potassium thiocyanate;
(4) a composition comprising:
(a) a first component comprising, per 100 grams:
(i) about 25.0 g of water;
(ii) about 0.75 IU of lactoperoxidase;
(iii) about 75.0 g of sorbitol; and
(iv) about 0.5 g of lactoferrin; and
(b) a second component comprising, per 100 grams:
(i) about 100 g of water; and
(ii) about 0.8 millimole of potassium iodate;
(5) a composition comprising:
(a) a first component comprising, per 100 grams:
(i) about 40.0 g of water;
(ii) about 10.0 IU of lactoperoxidase;
(iii) about 1.5 g of lysozyme; and
(iv) about 60.0 g of polyethylene glycol; and
(b) a second component comprising:
(i) about 100 g of water; and
(ii) about 0.9 millimole of potassium thiocyanate;
(6) a composition comprising:
(a) a first component comprising, per 100 grams:
(i) about 100 g of water;
(ii) about 80.0 IU of lactoperoxidase;
(iii) about 50.0 IU of glucose oxidase; and
(iv) about 20.0 g of glycerin; and
(b) a second component comprising, per 100 grams:
(i) about 100 g of water;
(ii) about 0.15 millimoles of β-D-glucose; and
(iii) about 0.1 millimoles of potassium iodate;
(7) a composition comprising:
(a) a first component comprising, per 100 grams:
(i) about 94.0 g of water;
(ii) about 5.0 g of glycerol;
(iii) about 1.0 g of potassium sorbate; and
(iv) about 0.75 IU of myeloperoxidase; and
(b) a second component comprising, per 100 grams:
(i) about 100 g of water; and
(ii) about 0.25 millimoles of sodium chlorate;
(8) a composition comprising:
(a) a first component comprising, per 100 grams:
(i) about 45.0 g of water;
(ii) about 100.0 IU of myeloperoxidase;
(iii) about 5000 IU of galactose oxidase; and
(iv) about 50.0 g of glycerol;
(b) a second component comprising, per 100 grams:
(i) about 100 g of water;
(ii) about 1.0 millimole of potassium thiocyanate; and
(iii) about 60 millimoles of D-galactose;
(9) a composition comprising:
(a) a first component comprising, per 100 grams:
(i) about 90.0 g of water;
(ii) about 50.0 IU of horseradish peroxidase; and
(iii) about 10.0 g of polypropylene glycol; and
(b) a second component comprising, per 100 grams:
(i) about 99.25 g of water;
(ii) about 0.001 millimole of potassium iodate; and
(iii) about 0.75 g of potassium ascorbate;

(10) a composition comprising:
(a) a first component comprising, per 100 grams:
(i) about 99.0 g of water;
(ii) about 1.0 g of glycerine;
(iii) about 50.0 millimole of choline; and
(iv) about 95.0 IU of lactoperoxidase; and
(b) a second component comprising, per 100 grams:
(i) about 100 g of water;
(ii) about 1000 IU of choline oxidase; and
(iii) about 0.6 millimole of potassium thiocyanate;
(11) a composition comprising:
(a) a first component comprising, per 100 grams:
(i) about 100 g of glycerin; and
(ii) about 3000 IU of lactoperoxidase; and
(b) a second component comprising, per 100 grams:
(i) about 100 g of water; and
(ii) about 0.6 millimole of potassium iodate;
(12) a composition comprising:
(a) a first component comprising, per 100 grams:
(i) about 80.0 g of water;
(ii) about 20.0 g of sorbitol; and
(iii) about 5.0 IU of lactoperoxidase; and
(b) a second component comprising, per 100 grams:
(i) about 80.0 g of water;
(ii) about 20.0 g of glycerol; and
(iii) about 0.0001 millimole of potassium thiocyanate; and
(13) a composition comprising:
(a) a first component comprising, per 100 grams:
(i) about 75.0 g of water;
(ii) about 25.0 g of glycerol;
(iii) about 2000 IU of lactoperoxidase;
(iv) about 1000 IU of horseradish peroxidase;
(v) about 0.01 g of sodium ascorbate;
(vi) about 0.05 g of ferrous sulfate; and
(vii) about 0.25 IU of glucose oxidase; and
(b) a second component comprising, per 100 grams:
(i) about 75.0 g of water;
(ii) about 25.0 g of glycerol;
(iii) about 0.05 millimole of potassium iodate; and
(iv) about 40.0 millimole of β-D-glucose.

Another aspect of the invention is a method of use of a composition according to the present invention to treat a lung disease or condition in a patient in need thereof. In general, this method comprises the step of administering a composition according to the present invention to a patient suffering from a lung disease or condition by a route in which the ingredients of the composition reach the lungs and generate the biocide within the lungs to treat the lung disease or condition.

In one alternative, the disease or condition is pneumonia, such as pneumococcal pneumonia, streptococcal pneumonia, staphylococcal pneumonia, pneumonia caused by infection with *Haemophilus*, or mycoplasmal pneumonia. Alternatively, the disease or condition is acute respiratory failure or acute respiratory distress syndrome.

Typically, the composition is introduced into the lungs via a ventilator, vaporizer, or nebulizer.

DETAILED DESCRIPTION OF THE INVENTION

One embodiment of the present invention is a therapeutic composition comprising:
(1) a first component comprising:
(a) one of:
(i) an oxidoreductase enzyme that produces hydrogen peroxide by catalyzing the oxidation of a substrate for which the oxidreductase enzyme is specific, the first component comprising a sufficient quantity of the oxidoreductase enzyme that a quantity of hydrogen peroxide sufficient to react with a peroxidase is produced; and
(ii) a substrate that is oxidizable in a reaction catalyzed by the oxidoreductase enzyme in a sufficient quantity that a quantity of hydrogen peroxide sufficient to react with a peroxidase is produced;
(b) a peroxidase enzyme that catalyzes a reaction between hydrogen peroxide and a salt that acts as an oxygen acceptor and is capable of reacting with hydrogen peroxide to form a biocide, the peroxidase enzyme being present in a sufficient quantity such that the biocide is produced in a therapeutically effective concentration; and
(c) an aqueous or nonaqueous medium in which the enzymes and the oxidizable substrate, if present, are stable; and
(2) a second component comprising:
(a) the other of the oxidoreductase enzyme and the substrate that is oxidizable in a reaction catalyzed by the oxidoreductase enzyme that is not present in (1); and
(b) a salt that acts as an oxygen acceptor and is capable of reacting with hydrogen peroxide to form a biocide in a quantity sufficient to form a therapeutically effective concentration of the biocide; and
(c) an aqueous or nonaqueous medium in which the other of the oxidoreductase enzyme and the oxidizable substrate and the salt that acts as an oxygen acceptor are stable, with the proviso that one of the media of the first component and the second component is aqueous. This embodiment is particularly suitable for the treatment of diseases and conditions such as those caused by fungus in which there is no additional endogenous hydrogen peroxide or only a minimal quantity of endogenous hydrogen peroxide produced by the disease process. In this embodiment, therefore, an oxidizable substrate and an oxidoreductase enzyme specific for the substrate is added in order to ensure an adequate amount of hydrogen peroxide to create an effective quantity of biocide.

Typically, the composition comprises from about 0.5 to about 500 International Units of the oxidoreductase enzyme. Typically, the composition comprises from about 0.015 to about 0.6 millimole of the oxidizable substrate. Typically, the composition comprises from about 0.05 to about 30 International Units of the peroxidase enzyme. Typically, the composition comprises from about 0.0001 to about 0.01 millimole of the salt that acts as an oxygen acceptor.

In one alternative, the media of the first and second component are both aqueous media. In another alternative, the medium of the first component can be a nonaqueous medium such as glycerol. As used herein, the term "aqueous" does not exclude nonaqueous ingredients such as glycerol or sorbitol, as long as a significant proportion of water is present in the medium.

Ingredients can be interchanged between the first and second components, as shown below in the Examples. For example, the substrate that is oxidizable in a reaction catalyzed by the oxidoreductase enzyme can be included in the first component, and the oxidoreductase enzyme can be included in the second component.

More than one peroxidase enzyme can be included. For example, the first component can comprise both lactoperoxidase and horseradish peroxidase. Other combinations of peroxidases can be used.

The first component and the second component can be prepared separately and mixed before use.

As used herein, the term International Unit (IU) is defined as the quantity of enzyme that catalyzes the conversion of one micromole of substrate per minute under defined standard assay conditions for that enzyme.

The oxidoreductase enzyme is typically selected from the group consisting of glucose oxidase, galactose oxidase, urate oxidase, choline oxidase, D-amino acid oxidase, D-glutamate oxidase, glycine oxidase, glycolic oxidase, L-sorbose oxidase, alcohol oxidase, and amine oxidase. Other enzymes can alternatively be used, such as nitroethane oxidase, D-aspartate oxidase, L-amino acid oxidase, pyridoxamine phosphate oxidase, ethanolamine oxidase, pyruvate oxidase, oxalate oxidase, hexose oxidase, cholesterol oxidase, aryl alcohol oxidase, pyridoxine 4-oxidase, dehydroorotate oxidase, lathosterol oxidase, sarcosine oxidase, N-methylaminoacid oxidase, $N^6$-methyllysine oxidase, 6-hydroxy-L-nicotine oxidase, 6-hydroxy-D-nicotine oxidase, 3-hydroxyanthranilate oxidase, aldehyde oxidase, and xanthine oxidase, as described in U.S. Pat. No. 4,340,448 to Schiller et al., incorporated herein by this reference.

For these enzymes, glucose oxidase catalyzes the reaction of β-D-glucose, water, and oxygen to produce hydrogen peroxide and gluconic acid. Galactose oxidase catalyzes the reaction of D-galactose and oxygen to produce hydrogen peroxide and D-galacto-hexodialdose. Urate oxidase catalyzes the reaction of uric acid, water, and oxygen to produce hydrogen peroxide, allantoin, and carbon dioxide. Choline oxidase catalyzes the reaction of choline and oxygen to produce hydrogen peroxide and betaine aldehyde. D-amino acid oxidase catalyzes the reaction of D-amino acids such as D-proline, D-methionine, D-isoleucine, D-alanine, D-valine, or D-phenylalanine with water and oxygen to produce hydrogen peroxide, ammonia, and the α-keto acid corresponding to the D-amino acid being oxidized. D-glutamate oxidase catalyzes the reaction of D-glutamic acid, water, and oxygen to produce hydrogen peroxide, ammonia, and 2-ketoglutarate. Glycine oxidase catalyzes the reaction of glycine, water, and oxygen to produce hydrogen peroxide, ammonia, and glyoxylic acid. Glycolic acid oxidase (also known as 2-hydroxyacid oxidase) catalyzes the reaction of glycolic acid and oxygen to produce 2-ketoacetic acid and hydrogen peroxide. L-sorbose oxidase catalyzes the reaction of L-sorbose and oxygen to produce 5-dehydro-D-fructose and hydrogen peroxide. Alcohol oxidase catalyzes the reaction of a lower primary alcohol or an unsaturated alcohol and oxygen to produce the corresponding aldehyde and hydrogen peroxide. Amine oxidase catalyzes the reaction of an amine, typically a primary amine, but also, in some cases, a secondary or tertiary amine, water, and oxygen to produce the corresponding aldehyde, ammonia, and hydrogen peroxide. In an illustrative reaction, glucose oxidase catalyzes the reaction of β-D-glucose, water, and oxygen during application to the outer ear to produce hydrogen peroxide and gluconic acid.

The peroxidase enzyme is typically one of lactoperoxidase, horseradish peroxidase, myeloperoxidase, eosinophil peroxidase, and glutathione peroxidase.

The salt that acts as an oxygen acceptor and is capable of reacting with hydrogen peroxide to form a biocide is typically an alkali metal salt of an anion such as thiocyanate, iodate, or chlorate. The alkali metal salt is typically a sodium or potassium salt, although other alkali metal salts such as lithium or cesium can alternatively be used.

The properties of a number of preferred oxidases suitable for use in compositions according to the present invention are known. For example, glucose oxidase from *Aspergillus niger* has been determined to have a molecular weight of 150,000 (Pazur et al. (1965)). The enzyme is a glycoprotein containing two molecules of the redox coenzyme flavin adenine dinucleotide (FAD). The amino acid composition has been determined. The isoelectric point of the enzyme is 4.2. The optimum pH of the enzyme is 5.5 with a broad pH range of from 4 to 7. Inhibitors of the enzyme include monovalent silver ions and divalent mercury and copper ions.

Galactose oxidase from *Dactylium dendroides* has a molecular weight of 42,000. It is a metalloenzyme containing one gram-atom of copper per mole. The amino acid composition has been determined. The optimum pH of the enzyme is 7.

Urate oxidase (uricase) from hog liver or beef liver has a molecular weight of 100,000. It is a metalloenzyme containing one gram-atom of copper per mole. The isoelectric point of the enzyme is 6.3. The optimum pH of the enzyme is 9.

D-amino acid oxidase from hog kidney has a molecular weight of 90,000. The enzyme is a glycoprotein containing two molecules of flavin adenine dinucleotide. The optimum pH of the enzyme is 9.1. Certain heavy metals are inhibitors of the enzyme.

The oxidizable substrate is typically present in the therapeutic composition at a concentration of from about 0.015 millimoles per milliliter of liquid to about 0.6 millimoles per gram of composition. Preferably, the oxidizable substrate is present in the therapeutic composition at a concentration of from about 0.025 millimoles per gram of composition to about 0.1 millimole per gram of composition. The salt that acts as an oxygen acceptor is typically present in the therapeutic composition at a concentration of from about 0.0001 millimole to about 0.01 millimole per gram of composition. The salt that acts as an oxygen acceptor is preferably present in the therapeutic composition at a concentration of from about 0.001 millimole to about 0.006 millimole per gram of composition.

Typically, the oxidoreductase enzyme is present in the therapeutic composition in a concentration of from about 0.5 IU to about 500 IU gram of composition. Preferably, the oxidoreductase enzyme is present in the therapeutic composition in a concentration of from about 10 IU to about 40 IU per gram of composition. Oxidoreductase enzymes are supplied in dry or liquid form with the label specifying the concentration in International Units on a per gram or per milliliter basis, as appropriate.

As indicated above, the therapeutic composition according to the present invention is also provided with a second enzyme. The second enzyme is a peroxidase. A suitable peroxidase is lactoperoxidase. Lactoperoxidase is a glycoprotein which, in one commercial embodiment, is a lyophilized powder derived from milk. This commercial peroxidase has an activity of 80 IU/mg and a projected molecular weight of 93,000 for L-tyrosine iodination. The physicochemical properties reported for lactoperoxidase include a molecular weight of 78,000, a partial specific volume, reflective of the amino acid composition, of 0.74, and the presence of 1.0 mole of heme per mole of lactoperoxidase. As indicated above, other peroxidases, including, but not limited to, horseradish peroxidase, myeloperoxidase, eosinophil peroxidase, and glutathione peroxidase, can alternatively be used.

The peroxidase is typically present in the therapeutic composition in a concentration of from about 0.05 IU to about 30 IU per gram of composition; preferably, the peroxidase is present in the therapeutic composition in a concentration of from about 0.1 IU to about 1.0 IU per gram of composition.

The operable integrity of the enzymatic system can be affected by the presence of catalase, which is present in commercial glucose oxidase as well as in mucous membrane tissue. Catalase, which is extraneous to the enzymatic system of this invention, competes with peroxidase for hydrogen peroxide. In order to reduce the loss of hydrogen peroxide through the presence of catalase, an effective amount of an enzymatic inhibitor that is specific for catalase can be advantageously incorporated into a therapeutic composition according to the present invention. Suitable enzymatic inhibitors specific for catalase include, but are not limited to ascorbic salts such as sodium ascorbate, potassium ascorbate, calcium ascorbate, ascorbyl palmitate, or mixtures thereof, and can be included in a therapeutic composition according to the invention. An effective concentration of ascorbic salt in compositions according to the present invention is from about $1\times10^{-6}$ to about $1\times10^{-4}$ millimole per gram of therapeutic composition. Iron salts such as ferrous sulfate, ferrous chloride, or ferrous iodide can also be incorporated into a therapeutic composition according to the present invention as a potentiator for the ascorbic salt in its role as catalase inhibitor. A particularly preferred iron salt is ferrous sulfate.

Therapeutic compositions according to the present invention can also advantageously be formulated with an aminohexose in order to increase the yield or accumulation of oxidized anionic biocidal agent, the quantity of the aminohexose being effective to increase the yield or accumulation of oxidized anionic biocidal agent. Typically, the aminohexose is an aminoglucose, but other aminohexoses such as aminogalactose can alternatively be used. Typically, the aminoglucose is selected from the group consisting of glucosamine, N-acetylglucosamine, and mixtures thereof. The aminoglucose is typically present in the therapeutic composition in a concentration of from about 0.0001 millimole to about 0.002 millimole per gram of composition. Preferably, the aminoglucose is present in the therapeutic composition in a concentration of from about 0.0003 millimole to about 0.001 millimole per gram of composition.

The media described above typically are each independently selected from the group consisting of water, glycerol, sorbitol, propylene glycol, and mixtures thereof, with the proviso that at least one of the media includes a substantial proportion of water. As used herein, the term “substantial proportion of water” is defined as a sufficient quantity of water when the two components are mixed so that ions can be efficiently solvated and that enzymatic reactions that require the participation of ionic species can proceed efficiently. In addition, nonaqueous media can include solvents with substantially equivalent properties that are non-denaturing with respect to the enzymes and serve as suitable media for catalysis of the reactions catalyzed by the enzymes. The media are typically present in the composition in a total concentration from about 80 weight percent to about 96 weight percent. Preferably, the media are present in the composition in a total concentration from about 90 weight percent to about 96 weight percent. The media and the concentration thereof are selected such as to provide the composition with appropriate pressure responsive application characteristics.

In some alternatives, the products of the activated enzyme system of the therapeutic composition include a weak organic acid, such as gluconic acid. In this case, it is advantageous to formulate the composition with a buffering agent in order to neutralize the organic acid. Suitable buffering agents include, but are not limited to, salts of stearic acid such as sodium stearate, potassium stearate, or calcium stearate. A particularly preferred salt of stearic acid is sodium stearate. These salts can be present in the composition in a concentration of up to about 6.0 weight percent. Typically, the salt is present in the composition in an amount of from about 2.0 weight percent to about 6.0 weight percent. Citric acid can also be used as a buffering agent.

The composition can further include a salt of sorbic acid such as sodium sorbate or potassium sorbate. A preferred salt of sorbic acid is potassium sorbate.

Adjunct therapeutic agents such as the enzyme lysozyme, the protein lactoferrin, and an anti-inflammatory medication such as a steroid, including, but not limited to, hydrocortisone, beclomethasone, budenoside, ciclesonide, flunisolide, fluticasone, methylprednisolone, prednisolone, prednisone, and triamcinolone, as well as the salts, solvates, analogues, congeners, bioisosteres, hydrolysis products, metabolites, precursors, and prodrugs thereof, can be added to the enzymatic formulations of this invention. A particularly preferred steroid is hydrocortisone.

Other ingredients generally known in the pharmaceutical art can be incorporated into therapeutic compositions according to the present invention, including colorants, chelating agents, preservatives, and stabilizers, with the proviso that these additional ingredients do not inhibit the oxidation-reduction reactions on which the activity of the compositions according to the present invention depend.

The di-enzymatic therapeutic composition in the form of a flowable liquid can be prepared in any suitable manner as, for example, by blending the dry ingredients into the liquid ingredients, with agitation, until a uniform mixture is obtained, with the proviso that shear sensitive ingredients, which include the enzymes are added last to minimize shear impact on these ingredients. When the enzymes are added, extremes of temperature, pH, and ionic strength, which have a tendency to denature proteins, including enzymes, are to be avoided. Following formulation of the compositions, the flowable liquid can be used as described below. For example, the liquid can be loaded into a suitable dispenser for application.

In another embodiment of the invention, the oxidoreductase enzyme and the substrate that is oxidizable are omitted. In this embodiment, the composition includes the peroxidase enzyme and the salt that acts as an oxygen acceptor, and the composition acts by degrading endogenous hydrogen peroxide, such as occurs in the lungs.

In general, this embodiment of the composition comprises:

(1) a peroxidase enzyme that catalyzes a reaction between hydrogen peroxide and a salt that acts as an oxygen acceptor and is capable of reacting with hydrogen peroxide to form a biocide, the peroxidase enzyme being present in a sufficient quantity such that the biocide is produced in a therapeutically effective concentration;

(2) a salt that acts as an oxygen acceptor and is capable of reacting with hydrogen peroxide to form a biocide in a quantity sufficient to form a therapeutically effective concentration of the biocide; and (3) an aqueous medium in which the peroxidase enzyme and the salt that acts as an oxygen acceptor are stable.

The peroxidase enzyme and the salt that acts as an oxygen acceptor are as described above.

In this alternative, typically, the composition comprises from about 0.05 to about 30 International Units of the peroxidase enzyme. Typically, the composition comprises from about 0.0001 to about 0.01 millimole of the salt that acts as an oxygen acceptor.

The composition can be formulated in two parts, as shown in the Examples. In this alternative, one of the parts contains the peroxidase enzyme and the other of the parts contains the salt that acts as an oxygen acceptor. In this alternative, one of the parts can include a nonaqueous medium, with the proviso that when the two parts are combined, the combined medium is aqueous. However, the medium can further include a non-aqueous solvent as described above, such as, but not limited to, glycerol, sorbitol, propylene glycol, or mixtures thereof.

As described above, this embodiment of the composition can further comprise an effective amount of an inhibitor that is effective for catalase. This embodiment of the composition can further comprise an iron salt, as described above. This embodiment of the composition can also further comprise a quantity of an aminohexose effective in increasing the yield or accumulation of biocide formed, as described above. This embodiment of the composition can also further comprise a buffering agent, as described above. In addition, this embodiment of the composition can further comprise any or all of lysozyme, lactoferrin, or a steroid, as described above.

Particular embodiments of the invention include, but are not limited to, a therapeutic composition selected from the group of:

(1) a composition comprising:
(a) a first component comprising, per 100 grams:
(i) about 80 g of water;
(ii) about 20 g of glycerol; and
(iii) about 5.0 IU of lactoperoxidase; and
(b) a second component comprising, per 100 grams:
(i) about 100 g of water; and
(ii) about 0.01 millimole of potassium thiocyanate;
(2) a composition comprising:
(a) a first component comprising, per 100 grams:
(i) about 95.0 g of water;
(ii) about 5.0 g of propylene glycol; and
(iii) about 25.0 IU of lactoperoxidase; and
(b) a second component comprising, per 100 grams:
(i) about 100 g of water; and
(ii) about 0.1 millimole of potassium iodate;
(3) a composition comprising:
(a) a first component comprising, per 100 grams:
(i) about 50.0 g of water;
(ii) about 100.0 IU of lactoperoxidase;
(iii) about 49.5 g of glycerol; and
(iv) about 0.5 g of citric acid;
(b) a second component comprising, per 100 grams:
(i) about 100 g of water; and
(ii) about 1.0 millimole of potassium thiocyanate;
(4) a composition comprising:
(a) a first component comprising, per 100 grams:
(i) about 25.0 g of water;
(ii) about 0.75 IU of lactoperoxidase;
(iii) about 75.0 g of sorbitol; and
(iv) about 0.5 g of lactoferrin; and
(b) a second component comprising, per 100 grams:
(i) about 100 g of water; and
(ii) about 0.8 millimole of potassium iodate;
(5) a composition comprising:
(a) a first component comprising, per 100 grams:
(i) about 40.0 g of water;
(ii) about 10.0 IU of lactoperoxidase;
(iii) about 1.5 g of lysozyme; and
(iv) about 60.0 g of polyethylene glycol; and
(b) a second component comprising:
(i) about 100 g of water; and
(ii) about 0.9 millimole of potassium thiocyanate;
(6) a composition comprising:
(a) a first component comprising, per 100 grams:
(i) about 100 g of water;
(ii) about 80.0 IU of lactoperoxidase;
(iii) about 50.0 IU of glucose oxidase; and
(iv) about 20.0 g of glycerin; and
(b) a second component comprising, per 100 grams:
(i) about 100 g of water;
(ii) about 0.15 millimoles of β-D-glucose; and
(iii) about 0.1 millimoles of potassium iodate;
(7) a composition comprising:
(a) a first component comprising, per 100 grams:
(i) about 94.0 g of water;
(ii) about 5.0 g of glycerol;
(iii) about 1.0 g of potassium sorbate; and
(iv) about 0.75 IU of myeloperoxidase; and
(b) a second component comprising, per 100 grams:
(i) about 100 g of water; and
(ii) about 0.25 millimoles of sodium chlorate;
(8) a composition comprising:
(a) a first component comprising, per 100 grams:
(i) about 45.0 g of water;
(ii) about 100.0 IU of myeloperoxidase;
(iii) about 5000 IU of galactose oxidase; and
(iv) about 50.0 g of glycerol;
(b) a second component comprising, per 100 grams:
(i) about 100 g of water;
(ii) about 1.0 millimole of potassium thiocyanate; and
(iii) about 60 millimoles of O-galactose;
(9) a composition comprising:
(a) a first component comprising, per 100 grams:
(i) about 90.0 g of water;
(ii) about 50.0 IU of horseradish peroxidase; and
(iii) about 10.0 g of polypropylene glycol; and
(b) a second component comprising, per 100 grams:
(i) about 99.25 g of water;
(ii) about 0.001 millimole of potassium iodate; and
(iii) about 0.75 g of potassium ascorbate;
(10) a composition comprising;
(a) a first component comprising, per 100 grams:
(i) about 99.0 g of water;
(ii) about 1.0 g of glycerine;
(iii) about 50.0 millimole of choline; and
(iv) about 95.0 IU of lactoperoxidase; and
(b) a second component comprising, per 100 grams:
(i) about 100 g of water;
(ii) about 1000 IU of choline oxidase; and
(iii) about 0.6 millimole of potassium thiocyanate;
(11) a composition comprising:
(a) a first component comprising, per 100 grams:
(i) about 100 g of glycerin; and
(ii) about 3000 IU of lactoperoxidase; and
(b) a second component comprising, per 100 grams:
(i) about 100 g of water; and
(ii) about 0.6 millimole of potassium iodate;
(12) a composition comprising:
(a) a first component comprising, per 100 grams:
(i) about 80.0 g of water;
(ii) about 20.0 g of sorbitol; and
(iii) about 5.0 IU of lactoperoxidase; and
(b) a second component comprising, per 100 grams:
(i) about 80.0 g of water;
(ii) about 20.0 g of glycerol; and
(iii) about 0.0001 millimole of potassium thiocyanate; and
(13) a composition comprising:
(a) a first component comprising, per 100 grams:
(i) about 75.0 g of water;
(ii) about 25.0 g of glycerol;
(iii) about 2000 IU of lactoperoxidase;
(iv) about 1000 IU of horseradish peroxidase;
(v) about 0.01 g of sodium ascorbate;
(vi) about 0.05 g of ferrous sulfate; and
(vii) about 0.25 IU of glucose oxidase; and (b) a second component comprising, per 100 grams:

(i) about 75.0 g of water;

(ii) about 25.0 g of glycerol;

(iii) about 0.05 millimole of potassium iodate; and (iv) about 40.0 millimole of β-D-glucose.

Another aspect of the invention is a method of use of a composition according to the present invention to treat a lung disease or condition in a patient in need thereof. In general, this method comprises the step of administering a composition according to the present invention to a patient suffering from a lung disease or condition by a route in which the ingredients of the composition reach the lungs and generate the biocide within the lungs to treat the lung disease or condition.

The composition can be introduced into the lungs via a ventilator, vaporizer, or nebulizer. Because the reaction between the enzymes, hydrogen peroxide, and the substrates is very rapid, typically, the composition is administered in two parts, the first component and the second component being administered separately. Otherwise the reaction can occur more strongly in the upper lung tracts but not strongly enough in the lower sections of the lungs.

Aerosol therapy allows an almost ideal benefit to risk ratio to be achieved because very small doses of inhaled medication provide optimal therapy with minimal adverse effects. However, the therapeutic efficiency of drugs administered by aerosolization depends not only on the pharmacological properties of the drugs themselves, but also on the characteristics of the delivery device. The characteristics of the delivery device influence the amount of drug deposited in the lungs and the pattern of drug distribution in the airways.

Aerosols are airborne suspensions of fine particles. The particles may be solids or liquids. Aerosol particles are heterodisperse (i.e. the particles are of a range of sizes) and aerosol particle size distribution is best described by a log normal distribution. Particles tend to settle (sediment), adhere to each other (coagulate), and adhere to structures such as tubing and mucosa (deposit). The particles delivered by aerosol can be conveniently characterized on the basis of their aerodynamic behavior. One parameter is the mass median aerodynamic diameter (MMAD). By definition, a particle distribution with an MMAD of 1 μM has the same average rate of settling as a droplet of unit density and 1 μM diameter.

The size of an aerosol particle, as well as variables affecting the respiratory system, influence the deposition of inhaled aerosols in the airways. On one hand, particles larger than 10 μM in diameter are unlikely to deposit in the lungs. However, particles smaller than 0.5 μM are likely to reach the alveoli or may be exhaled. Therefore, particles that have a diameter of between 1 μM and 5 μM are most efficiently deposited in the lower respiratory tract. Particles of these sizes are most efficient for the delivery of therapeutic agents for treatment of lung diseases or conditions.

The percentage of the aerosol mass contained within respirable droplets (i.e., droplets with a diameter smaller than 5 μM), depends on the inhalation device being used. Slow, steady inhalation increases the number of particles that penetrate the peripheral parts of the lungs. As the inhaled volume is increased, the aerosol can penetrate more peripherally into the bronchial tree. A period of breath-holding, on completion of inhalation, enables those particles that have penetrated to the lung periphery to settle into the airways via gravity. Increased inspiratory flow rates, typically observed in patients with acute asthma, result in increased losses of inhaled drug. This occurs because aerosol particles impact in the upper airway and at the bifurcations of the first few bronchial divisions. Other factors associated with pulmonary airway disease may also alter aerosol deposition.

In aerosol administration, the nose efficiently traps particles before their deposition in the lung; therefore, mouth breathing of the aerosolized particles is preferred. The aerosolized particles are lost from many sites. Generally, the amount of the nebulized dose reaching the small airways is 15%. In many cases, approximately 90% of the inhaled dose is swallowed and then absorbed from the gastrointestinal tract. The small fraction of the dose that reaches the airways is also absorbed into the blood stream. The swallowed fraction of the dose is, therefore, absorbed and metabolized in the same way as an oral formulation, while the fraction of the dose that reaches the airways is absorbed into the blood stream and metabolized in the same way as an intravenous dose.

When drugs are administered topically (via aerosol delivery to the lungs), the desired therapeutic effects depend on local tissue concentrations. Furthermore, factors influencing pulmonary absorption should be considered Therapeutic aerosols are commonly produced by atomization of liquids within jet nebulizers or by vibration of a standing pool of liquid (ultrasonic nebulization). Preformed aerosols may also be administered. Examples of the latter include MDIs and dry powder devices.

All jet nebulizers work via a similar operating principle, represented by the familiar perfume atomizer. A liquid is placed at the bottom of a closed container, and the aerosol is generated by a jet of air from either a compressor or a compressed gas cylinder passing through the device. Ultrasonic nebulizers produce an aerosol by vibrating liquid lying above a transducer at frequencies of about 1 mHz. This produces a cloud of particles that is carried out of the device to the patient by a stream of air. Aerosols varying in quantity, size and distribution of panicles can be produced by nebulizers, depending upon the design of the nebulizers and how it is operated. It should be noted that not all nebulizers have the required specifications (MMAD, flow, output) to provide optimum efficacy. A recent study compared the lung deposition from 4 nebulizers in healthy volunteers and showed that median lung aerosol deposition, expressed as percentages of the doses initially loaded into the nebulizers, ranged from 2 to 19%.

Metered dose inhalers (MDIs), because of their convenience and effectiveness, are probably the most widely used therapeutic aerosol used for inhaled drug delivery to outpatients. Most MDIs in current use contain suspensions of drug in propellant. There are 2 major components of an MDI: (i) the canister, a closed plastic or metal cylinder that contains propellant, active medication, and the metering chamber; and (ii) the actuator, a molded plastic container that holds the canister and directs the released aerosol towards the patient's airway.

Propellant mixtures are selected to achieve the vapor pressure and spray characteristics desired for optimal drug delivery. Chlorofluorocarbons were previously used, but non-chlorinated propellants are now employed because of environmental concerns. Finely divided particles of drug, usually less than 1 μM, are suspended in the pressurized (liquefied) propellant. To prevent the drug from coagulating, a surface active agent such as sorbitan oleate, lecithin or oleic acid is typically added; other surface active agents are known in the art. Metering chambers ordinarily contain 25 to 100 μL. The contents of the metering chamber are released when the canister is depressed into the actuator. Almost instantaneously, the propellants begin to evaporate, producing disintegration of the discharged liquid into particles that are propelled forward with great momentum. For optimal pulmonary drug deposition, the medication should be released at the beginning of a slow inspiration that lasts about 5 seconds and is followed by 10 seconds of breath-holding. Several inhalation aids have been designed to improve the effectiveness of a MDI. These are most useful in patients who have poor hand-to-breath coordination. A short tube (e.g. cones or spheres) may direct the aerosol straight into the mouth or collapsible bags may act as an aerosol reservoir holding particles in suspension for 3 to 5 seconds, during which time the patient can inhale the drug. However, when any of these devices is used, aerosol velocity upon entering the oropharynx is decreased and drug availability to the lungs and deposition in the oropharynx is decreased.

Among the diseases and conditions for which methods according to the present invention can be used are: (1) pneumonia, including pneumococcal pneumonia, streptococcal pneumonia, staphylococcal pneumonia, pneumonia caused by infection with *Haemophilus*, and mycoplasmal pneumonia; (2) acute respiratory failure; and (3) acute respiratory distress syndrome. Methods according to the present invention can also be used to treat other diseases and conditions in which an inflammatory response is present in lung tissue, including, but not limited to, cystic fibrosis, asthma, and lung cancer.

The exact formulation, route of administration and dosage, including the frequency of administration and quantity of therapeutic composition administered, can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and with the route of administration, as well as by pharmacokinetic considerations such as liver and kidney function. The severity of the condition may, for example, be evaluated, in part, by standard prognostic evaluation methods. Further, the dose and perhaps the dose frequency, will also vary according to the age, body weight, and response of the individual patient. A program comparable to that discussed above may be used in veterinary medicine.

The invention is illustrated by the following Examples. These Examples are included for illustrative purposes only, and are not intended to limit the invention.

EXAMPLE 1

All examples are in a total of 100 grams per part and include Part A and Part B.

Part A is 80 g of water, 20 g of glycerol, and 5.0 IU of lactoperoxidase. Part B is 100 g of water and 0.01 millimole of potassium thiocyanate. In this Example, the lactoperoxidase utilizes endogenous hydrogen peroxide in the lungs to create the antibacterial hypothiocyanite ion.

EXAMPLE 2

Part A is 95.0 g of water, 5 g of propylene glycol, and 25.0 IU of lactoperoxidase. Part B is 100.0 g of water and 0.1 millimole of potassium iodate. In this Example, the lactoperoxidase utilizes endogenous hydrogen peroxide in the lungs to create the antibacterial hypoiodite ion.

EXAMPLE 3

Part A is 50.0 g of water, 100.0 IU of lactoperoxidase, 49.5 g of glycerol, and 0.5 g of citric acid. Part B is 100.0 g of water and 1.0 millimole of potassium thiocyanate. In this formula citric acid is added as a mild buffering agent.

EXAMPLE 4

Part A is 25.0 g of water, 0.75 IU of lactoperoxidase, 75.0 g of sorbitol, and 0.5 g of lactoferrin. Part B is 100.0 g of water and 0.8 millimole of potassium iodate. In this Example lactoferrin is added as an additional antibacterial protein.

EXAMPLE 5

Part A is 40.0 g of water, 10.0 IU of lactoperoxidase, 1.5 g of lysozyme, and 60.0 g of polyethylene glycol. Part B is 100.0 g of water and 0.9 millimole of potassium thiocyanate. In this Example the antibacterial enzyme lysozyme is added.

EXAMPLE 6

Part A is 100.0 g of water, 80.0 IU of lactoperoxidase, 50.0 IU of glucose oxidase, and 20.0 g of glycerol. Part B is 100.0 g of water, 0.15 millimole of β-D-glucose, and 0.1 millimole of potassium iodate. In this Example, glucose oxidase and its substrate β-D-glucose have been added for an additional source of hydrogen peroxide.

EXAMPLE 7

Part A is 94.0 g of water, 5.0 g of glycerol, 1.0 g of potassium sorbate, and 0.75 IU of myeloperoxidase. Part B is 100 g of water and 0.25 millimole of sodium chlorate. In this Example the enzyme myeloperoxidase is used as the enzyme that catalyzes a reaction with peroxide to produce the biocidal anion.

EXAMPLE 8

Part A is 45.0 g of water, 100.0 IU of myeloperoxidase, 5000 IU of galactose oxidase, and 50.0 g of glycerol. Part B is 100.0 g of water, 1.0 mmole of potassium thiocyanate, and 60 millimole of D-galactose. In this Example, galactose oxidase and D-galactose are added as an additional source of hydrogen peroxide.

EXAMPLE 9

Part A is 90.0 g of water, 50.0 IU of horseradish peroxidase, and 10.0 g of polypropylene glycol. Part B is 99.25 g of water, 0.001 mmole of potassium thiocyanate, and 0.75 g of potassium ascorbate. In this Example, horseradish peroxidase is used as the enzyme that catalyzes a reaction with peroxide to produce the biocidal anion.

EXAMPLE 10

Part A is 99.0 g of water, 1.0 g of glycerol, 50.0 millimole of choline, and 95.0 IU of lactoperoxidase. Part B is 100.0 g of water, 1000 IU of choline oxidase, and 0.6 millimole of potassium thiocyanate. In this Example the choline has been put in Part A and the choline oxidase has been put in Part B.

This shows that the oxidoreductase enzyme and its substrate can be put in either Part A or Part B.

EXAMPLE 11

Part A is 100.0 g of glycerol and 3000 IU of lactoperoxidase. Part B is 100.0 g of water and 0.6 millimoles of potassium iodate. In this Example glycerol is the carrier for the lactoperoxidase enzyme in Part A.

EXAMPLE 12

Part A is 80.0 g of water, 20.0 g of sorbitol, and 5.0 IU of lactoperoxidase. Part B is 80.0 g of water, 20.0 g of glycerol, and 0.0001 millimoles of potassium thiocyanate. In this Example, the lactoperoxidase is at a higher concentration.

EXAMPLE 13

Part A is 75.0 g of water, 25.0 g of glycerol, 2000 IU of lactoperoxidase, 1000 IU of horseradish peroxidase, 0.01 g of sodium ascorbate, 0.05 g of ferrous sulfate, and 0.25 IU of glucose oxidase. Part B is 75.0 g of water, 25.0 g of glycerol, 0.05 millimoles of potassium iodate, and 40.0 millimoles of β-D-glucose. In this Example, there are two peroxidase enzymes in Part A.

ADVANTAGES OF THE INVENTION

Compositions and methods according to the present invention provide a new and effective means for treating a number of lung diseases and conditions, including pneumonia, acute respiratory failure, and acute respiratory distress syndrome, characterized by inflammation or microbial infection. These compositions and methods can be used together with antimicrobials where appropriate and enhance the antimicrobial effect of such drugs. They are effective whether the origin of the pneumonia is bacterial or mycoplasmal and even in cases in which antibiotic resistance exists. They also treat the inflammation that accompanies these conditions. They are well tolerated and can be used over a considerable period of time without side effects or contraindications.

The inventions illustratively described herein can suitably be practiced in the absence of any element or elements, limitation or limitations, not specifically disclosed herein. Thus, for example, the terms “comprising,” “including,” “containing,” etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

We claim:

1. A therapeutic composition consisting essentially of:

(a) a peroxidase enzyme being present in a sufficient quantity such that a biocide is produced in a therapeutically effective concentration;

(b) a salt wherein the salt is an alkali metal salt of an anion of thiocyanate, iodate and chlorate;

(c) an aqueous medium in which the peroxidase enzyme and the salt that acts as an oxygen acceptor are stable;

(d) a quantity of an aminohexose; and (e) an effective amount of each of lysozyme, lactoferrin and a steroid wherein the composition is formulated for administration to the lungs to treat an infection or condition therein selected from the group consisting of pneumonia, acute respiratory failure and acute respiratory distress syndrome in such a way that the ingredients of the composition reach the lungs and generate the biocide within the lungs, further wherein the hydrogen peroxide is a byproduct of the infection.

2. The composition of claim I wherein the peroxidase enzyme is selected from the group consisting of lactoperoxidase, myeloperoxidase, eosinophil peroxidase, and glutathione peroxidase.

3. The composition of claim 2 further comprising an additional peroxidase enzyme that is selected from the group consisting of lactoperoxidase, myeloperoxidase, eosinophil peroxidase, and glutathione peroxidase.

4. The composition of claim 1 wherein the composition further comprises an effective amount of an inhibitor that is specific for catalase.

5. The composition of claim 4 wherein the inhibitor that is specific for catalase is a salt of ascorbic acid.

6. The composition of claim 1 wherein the media are each independently selected from the group consisting of water, glycerol, sorbitol, propylene glycol, and mixtures thereof, with the proviso that at least one of the media includes a substantial proportion of water.

7. The composition of claim 1 wherein the composition further comprises a buffering agent.

8. The composition of claim 7 wherein the buffering agent is selected from the group consisting of sodium stearate, potassium stearate, and calcium stearate.

9. The composition of claim 8 wherein the buffering agent is sodium stearate.

* * * * *